United States Patent [19]

Lepage et al.

[11] Patent Number: 4,548,917

[45] Date of Patent: Oct. 22, 1985

[54] PROCESS FOR THE DISPROPORTIONATION OF SILANES

[75] Inventors: Jean-Luc Lepage, Sainte-Foy-les Lyon; Gerard Soula, Meyzieu, both of France

[73] Assignee: Rhone-Poulenc Specialites Chimiques, Courbevoie, France

[21] Appl. No.: 583,208

[22] Filed: Feb. 24, 1984

[30] Foreign Application Priority Data

Feb. 25, 1983 [FR] France ................................ 83 03089

[51] Int. Cl.⁴ .............................................. C07F 7/08
[52] U.S. Cl. ................................... 502/150; 502/172; 423/341; 423/347; 556/469
[58] Field of Search ................ 556/469; 423/341, 347; 502/150, 172

[56] References Cited

U.S. PATENT DOCUMENTS

| | | | |
|---|---|---|---|
| 2,627,451 | 2/1953 | Erickson et al. | 556/469 X |
| 2,735,861 | 2/1956 | Erickson et al. | 556/469 |
| 3,557,176 | 1/1971 | Bazouin et al. | 556/469 |
| 3,607,900 | 9/1971 | Hart | 556/469 |
| 3,627,501 | 12/1971 | Kruger | 556/469 X |
| 3,728,368 | 4/1973 | Bazouin et al. | 556/469 |
| 3,856,837 | 12/1974 | Chandra | 556/469 X |

*Primary Examiner*—Paul F. Shaver
*Attorney, Agent, or Firm*—Burns, Doane, Swecker & Mathis

[57] ABSTRACT

Silane, $SiH_4$, and diochlorosilane, particularly suitable for the preparation of silicon are readily obtained by disproportionating trichlorosilane to dichlorosilane and, ultimately silane by reacting:

(a) a silane containing at least one Si-H bond, of the general formula $R_nH_mSiX_{4-(n+m)}$ wherein R represents an alkyl or aryl group, x represents a halogen or an alkoxy group, n is an integer equal to 0, 1, 2 or 3 and m is an integer equal to 1, 2 or 3, and (b) a catalyst system comprising an ionic inorganic salt of the formula $M^+A^-$ and a compound capable of at least partially dissociating the salt by complexing its cation $M^+$.

21 Claims, No Drawings

PROCESS FOR THE DISPROPORTIONATION OF SILANES

BACKGROUND OF THE INVENTION

1. Field of the Invention

The present invention relates to a process for the disproportionation of silanes containing at least one Si—H bond and, more particularly, to an advantageous process for the disproportionation of trichlorosilane to obtain dichlorosilane and ultimately, where desired, silane.

2. Description of the Prior Art

It is of course well known that silane is a preferred starting material for the formation through decomposition of very pure silicon which is particularly valuable for the fabrication of semiconductor devices and/or photovoltaic devices (e.g., solar cells). It is also known that it is possible to obtain silane by the disproportionation of trichlorosilane in the presence of various catalysts according to the following reactions:

$$2HSiCl_3 \rightleftharpoons H_2SiCl_2 + SiCl_4 \tag{1}$$

$$2H_2SiCl_2 \rightleftharpoons H_3SiCl + HSiCl_3 \tag{2}$$

$$2H_3SiCl \rightleftharpoons SiH_4 + H_2SiCl_2 \tag{3}$$

Various catalysts for carrying out the above disproportionation reactions have been described in the literature. Thus, for example, French Pat. No. 2,096,605 proposes the use of tertiary amines; French Pat. Nos. 2,118,725 and 2,261,977 suggest the use of anion exchange resins to which tertiary amines or quaternary ammonium groups are bonded; French Pat. No. 2,290,447 describes the use of N-substituted pyrrolidones and French Pat. No. 2,290,448 describes the use of tetraalkylureas.

To obtain acceptable yields, the catalysts which have been heretofore recommended are required to be utilized in relatively large amounts or require that the disproportionation reaction be carried out at elevated temperatures.

SUMMARY OF THE INVENTION

Accordingly, a primary object of the present invention is to provide a novel advantageous catalyst system and silane disproportionation process which unexpectedly makes it possible to carry out the disproportionation of silanes utilizing relatively small amounts of catalyst at reduced, even at ambient, temperatures.

Another object of the present invention is to provide a process and catalyst system therefor which surprisingly allows for reaching the thermodynamic equilibrium of such silane disproportionation reactions very rapidly compared with previously known catalysts and processes.

These and other similar objects, advantages and features are accomplished according to the catalytic silane disproportionation processes and catalyst systems of the present invention as described in detail hereinbelow.

DETAILED DESCRIPTION OF THE INVENTION

More particularly, according to this invention, a process for the disproportionation of silanes containing at least one Si—H bond has been discovered which makes it possible to obtain high yields of the desired silanes while using lowered reaction temperature and reduced quantities of catalyst than heretofore possible said process comprising reacting (a) a silane containing at least one Si—H bond, of the general formula $R_nH_mSiX_{4-(n+m)}$ wherein R represents an alkyl or aryl group, X represents a halogen or an alkoxy group, n is an integer equal to 0, 1, 2 or 3 and m is an integer equal to 1, 2 or 3, and (b) a catalyst system comprising an ionic inorganic salt of the formula $M^+A^-$ and a compound which complexes or chelates the cation $M^+$ of said salt.

The silanes containing at least one Si—H bond used in the process of the invention are those corresponding to the formula $R_nH_mSiX_{4-(n+m)}$, in which n may have any of the values 0, 1, 2 or 3 and m any of the values 1, 2 or 3. Groups corresponding to R, when present, are selected from straight or branched chain alkyl of from about 1 to 6 carbon atoms and aryl of from 6 to 10 carbon atoms and preferably include methyl, ethyl, propyl, isopropyl and phenyl. The moiety is selected from among halogens, preferably, chlorine, and alkoxy groups of 1 to 6 carbon atoms and preferably represented by methoxy or ethoxy groups. In a preferred embodiment of the present invention, trichlorosilane, dichlorosilane, monochlorosilane, methyldichlorosilane, phenyldichlorosilane or ethyldichlorosilane, or a mixture thereof are utilized as the silanes to be disproportionated.

The ionic inorganic salts of the formula $M^+A^-$ used according to the invention may be selected from a variety of salts without restriction so long as same do not react with the silanes present in the reaction medium, and are chosen, for example, from among those in which $M^+$ represents an alkali metal, an alkaline earth metal or ammonium, and preferably: $Li^+$, $Na^+$, $K^+$, $Ca^{++}$ or $NH_4^+$, and those in which $A^-$ represents a halogen, $SCN^-$, $CN^-$ or $CO_3^{--}$, and most preferably: $Cl^-$, $Br^-$ or $I^-$.

In a first preferred embodiment of the invention, the compound which complexes the cation of the ionic inorganic salt is a sequestering agent of the formula:

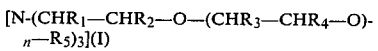

$$[N-(CHR_1-CHR_2-O-(CHR_3-CHR_4-O)_{n}-R_5)_3] \quad (I)$$

wherein n is an integer greater than or equal to 0 and less than or equal to 10 ($0 \leq n \geq 10$), $R_1$, $R_2$, $R_3$ and $R_4$, which may be identical or different, represent a hydrogen atom or an alkyl group having from about 1 to 4 carbon atoms and $R_5$ represents an alkyl or cycloalkyl group having from about 1 to 12 carbon atoms, a phenyl group or the group $-C_mH_{2m}-Ph$ (Ph=phenyl) or $C_mH_{2m+1}-Ph-$, where m is an integer between 1 and 12 ($1 \leq m \geq 12$).

In a second preferred method of practicing the invention, the complexing compound is a macrocyclic polyether comprising from 15 to 30 atoms in the ring and containing from 4 to 10 of the units —O—X, in which X may represent $-CHR_6-CHR_7-$ or $-CHR_6-CH R_8-CR_9R_7-$, $R_6$, $R_7$, $R_8$ and $R_9$, which may be identical or different, represent a hydrogen atom or an alkyl group having from 1 to 4 carbon atoms, with the further understanding that at least one of the symbols X may be $-CHR_6-CHR_8-CR_9R_7-$ when the —O—X units comprise the group $-O-CHR_6-CHR_7-$.

In a third embodiment for practicing the present invention, the complexing compound comprises a macrocyclic or bicyclic compound of the general formula IIa or IIb

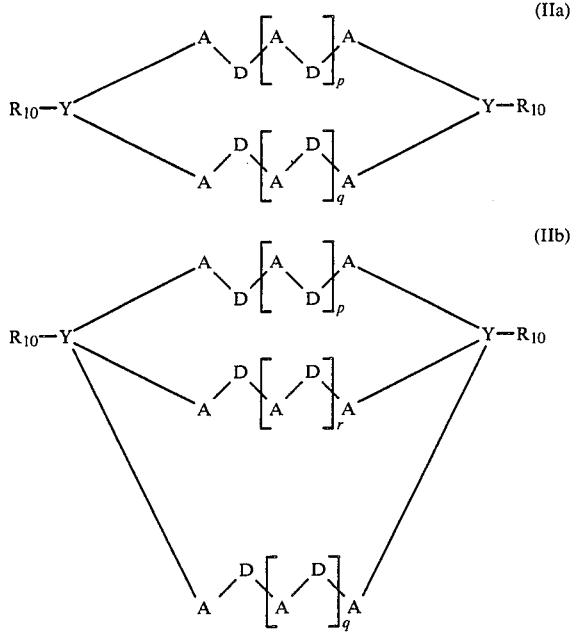

in which formulae:
Y represents N or P atoms,
A represents an alkylene group having from 1 to 3 carbon atoms,
D represents O, S or N—$R_{11}$, wherein $R_{11}$ represents an alkyl group having from 1 to 6 carbon atoms,
$R_{10}$ represents an alkyl group having from 1 to 6 carbon atoms, and
p, q and r, which are identical or different, are integers between 1 and 5.

In a fourth particular method of practicing the invention, a mixture of at least two of the complexing compounds defined above is used.

In another embodiment of the invention the complexing compounds used are sequestering agents, macrocyclic polyethers (also generally referred to as "crown ethers") and macrocyclic or bicyclic compounds (also known as "cryptands") grafted onto crosslinked organic polymeric supports. These graft complexing compounds are, for example, those described in European Patent Application No. 46,706 in the case of graft sequestering agents, and those described in the article Angew. Chem. Int. Ed. Engl. 18, 421–429 (1979) in the case of graft crown ethers or cryptands.

The graft type sequestering agents described in European Patent Application No. 46,706 are characterized in that they comprise a crosslinked organic polymeric support and a plurality of functional groups grafted (bonded) to the support as depicted in the general formula (III) below:

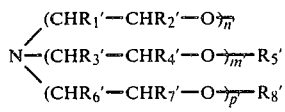

wherein $R_1'$, $R_2'$, $R_3'$, $R_4'$, $R_6'$ and $R_7'$, which may be identical or different, each independently represent a hydrogen atom or an alkyl group having from 1 to 4 carbon atoms and $R_5'$ and $R_8'$, which may be identical or different, independently represent a hydrogen atom, an alkyl or cycloalkyl group having from 1 to 12 carbon atoms, a phenyl group or the groups —$C_{q'}H_{2q'}$—Ph or $C_{q'}H_{2q'+1}$—Ph—, with q' being greater than or equal to 1 and less than or equal to about 12, and n', m' and p', which may be identical or different, are greater than or equal to 1 and less than or equal to 10.

Although it has not been entirely demonstrated, and without wishing to be bound to any particular theory relative to the present invention, it would appear that the compound which complexes the cation M+ of the ionic inorganic salt enables the salt to dissociate and be at least partially solubilized in the reaction medium.

Further, again without wishing to be bound by any particular theory, by way of technical elucidation, it may be considered that the disproportionation reaction mechanism of the present invention proceeds as follows: the anion A⁻ originating from the dissociated ionic inorganic salt present in the reaction medium coordinates with a silicon atom of a silane molecule to produce a hydride ion, H⁻, which in turn reacts with another silane molecule to generate an anion X⁻, and this in turn coordinates with a silicon atom to produce another hydride ion, H⁻, the process then continuing with the other silane molecules in the manner just described.

Thus, for example, if trichlorosilane is used, the reaction process can be represented by the following scheme:

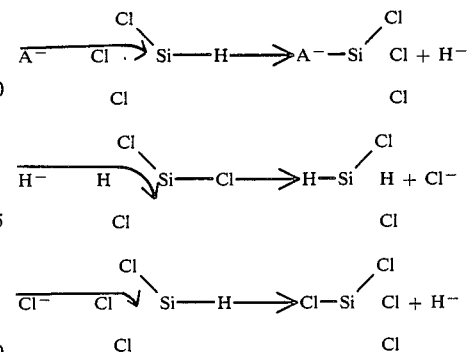

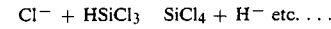

It should be noted that the foregoing reaction process is completely specific for the catalyst system containing the salt associated with the complexing compound. In fact, the ionic inorganic salt considered alone is not capable of catalyzing the disproportionation reaction.

In a specific preferred embodiment of the invention wherein a sequestering agent of the formula (I) above is employed, $R_1$, $R_2$, $R_3$ and $R_4$ represent a hydrogen atom or a methyl group with $R_5$ and n having the meanings set forth previously.

Among these sequestering agents, even more particularly preferred, are those wherein n is greater than or equal to 0 or less than or equal to 6 and in which $R_5$ represents an alkyl group having from 1 to 4 carbon atoms represented by the following:

tris-(3-oxabutyl)-amine of the formula:

$$N\text{—}(CH_2\text{—}CH_2\text{—}O\text{—}CH_3)_3$$

tris-(3,6-dioxaheptyl)-amine of the formula:
$$N\text{—}(CH_2\text{—}CH_2\text{—}O\text{—}CH_2\text{—}CH_2\text{—}O\text{—}CH_3)_3$$

tris-(3,6,9-trioxadecyl)-amine of the formula:
$$N\text{-}(CH_2\text{—}CH_2\text{—}O\text{—}CH_2\text{—}CH_2\text{—}O\text{—}CH_2\text{—}CH_2\text{—}O\text{—}CH_3)_3$$

tris-(3,6-dioxaoctyl)-amine of the formula:
$$N\text{—}(CH_2\text{—}CH_2\text{—}O\text{—}CH_2\text{—}CH_2\text{—}O\text{—}C_2H_5)_3$$

tris-(3,6,9-trioxaundecyl)-amine of the formula:
$$N\text{—}(CH_2\text{—}CH_2\text{—}O\text{—}CH_2\text{—}CH_2\text{—}O\text{—}CH_2\text{—}CH_2\text{—}O\text{—}C_2H_5)_3$$

tris-(3,6-dioxanonyl)-amine of the formula:

$$N\text{—}(CH_2\text{—}CH_2\text{—}O\text{—}CH_2\text{—}CH_2\text{—}O\text{—}C_3H_7)_3$$

tris-(3,6,9-trioxadodecyl)-amine of the formula:

$$N\text{—}(CH_2\text{—}CH_2\text{—}O\text{—}CH_2\text{—}CH_2\text{—}O\text{—}CH_2\text{—}CH_2\text{—}O\text{—}C_3H_7)_3$$

tris-(3,6-dioxadecyl)-amine of the formula:

$$N\text{—}(CH_2\text{—}CH_2\text{—}O\text{—}CH_2\text{—}CH_2\text{—}O\text{—}C_4H_9)_3$$

tris-(3,6,9-trioxatridecyl)-amine of the formula:

$$N\text{—}(CH_2\text{—}CH_2\text{—}O\text{—}CH_2\text{—}CH_2\text{—}O\text{—}CH_2\text{—}CH_2\text{—}O\text{—}C_4H_9)_3$$

tris-(3,6,9,12-tetraoxatridecyl)-amine of the formula:

$$N\text{—}(CH_2\text{—}CH_2\text{—}O\text{—}(CH_2\text{—}CH_2\text{—}O)_3\text{—}CH_3)_3$$

tris-(3,6,9,12,15,18-hexaoxanonadecyl)-amine of the formula:

$$N\text{—}(CH_2\text{—}CH_2\text{—}O\text{—}(CH_2\text{—}CH_2\text{—}O\text{—})_5\text{—}CH_3)_3$$

tris-(3,6-dioxa-4-methylheptyl)-amine of the formula:

$$N\text{—}(CH_2\text{—}CH_2\text{—}OCH\text{—}(CH_3)\text{—}CH_2\text{—}O\text{—}CH_3)_3$$

tris-(3,6,-dioxa-2,4-dimethylheptyl)-amine of the formula:

$$N\text{—}(CH_2CH\text{—}(CH_3)\text{—}OCH(CH_3)\text{—}CH_2\text{—}O\text{—}CH_3)_3.$$

The foregoing sequestering agents can be facilely prepared as described in French Pat. No. 2,450,120.

The foregoing amines are known entities, but not in the methods of the present invention. Thus, French Patent No. 1,302,365 mentions that, for example, the tertiary amines $N\text{—}(CH_2\text{—}CH_2\text{—}O\text{—}CH_3)_3$ and $N\text{—}(CH_2\text{—}CH_2\text{—}O\text{—}CH_2\text{—}CH_2\text{—}O\text{—}CH_3)_3$ are obtained as by-products in the synthesis of the corresponding primary and secondary amines and the primary and secondary amine products are valuable as intermediates for the synthesis of pharmaceuticals, as corrosion inhibitors, as intermediates for the synthesis of chemical products valuable in agriculture, and as emulsifiers. It is noted, however, that these fields of application of the compounds obtained in the abovementioned French Pat. No. 1,302,365 are not related to the field of the present invention pertaining to the use of such amines in the catalytic disproportionation of silanes.

The macrocyclic polyethers (crown ethers) which can be used in the process according to the invention are described for example in French Pat. No. 2,026,481.

The following may be mentioned as examples of crown ethers which can be advantageously used in accordance with the present invention:

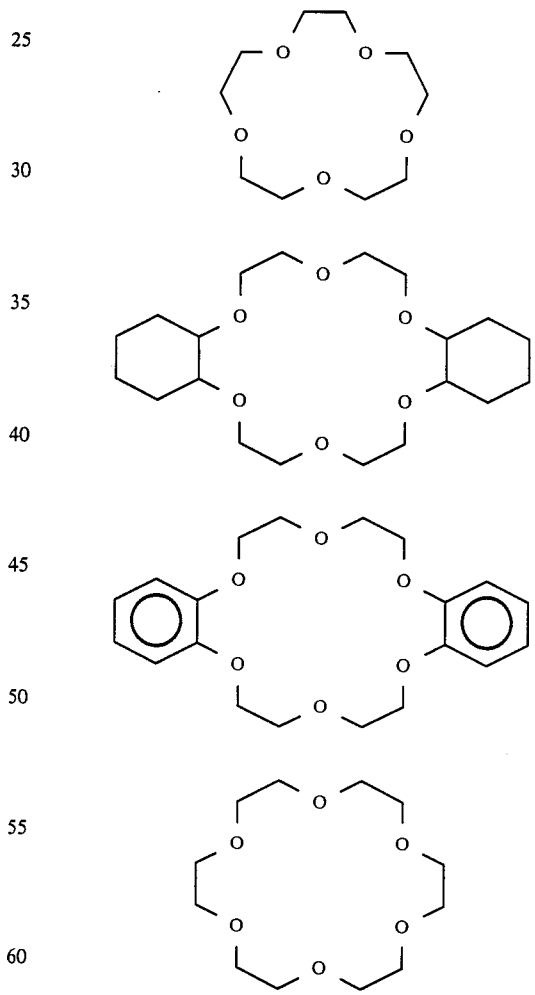

The macrocyclic and bicyclic compounds set forth hereinabove are described in French Pat. No. 2,052,947 and the following may be mentioned as examplary of such compounds for effectuating the process according to the invention:

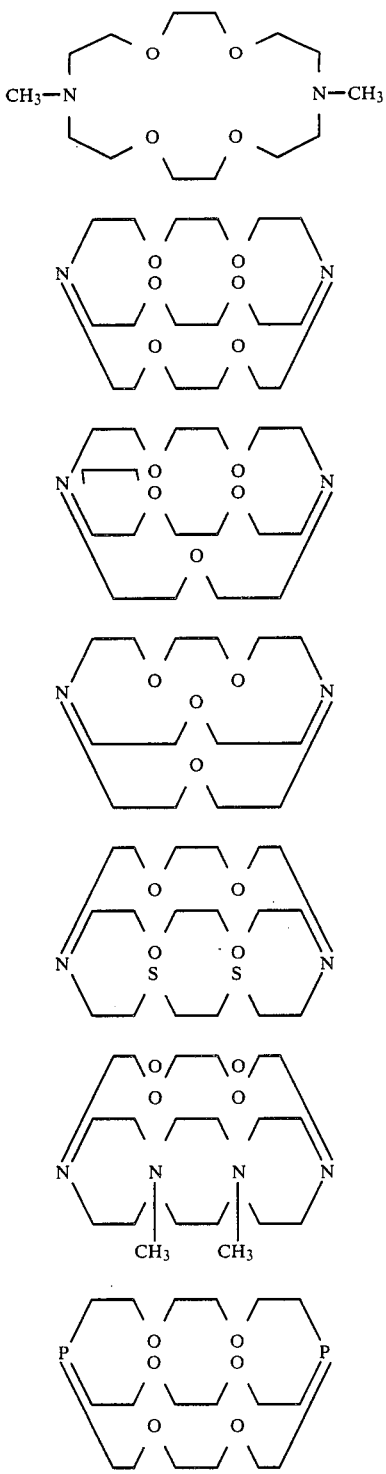

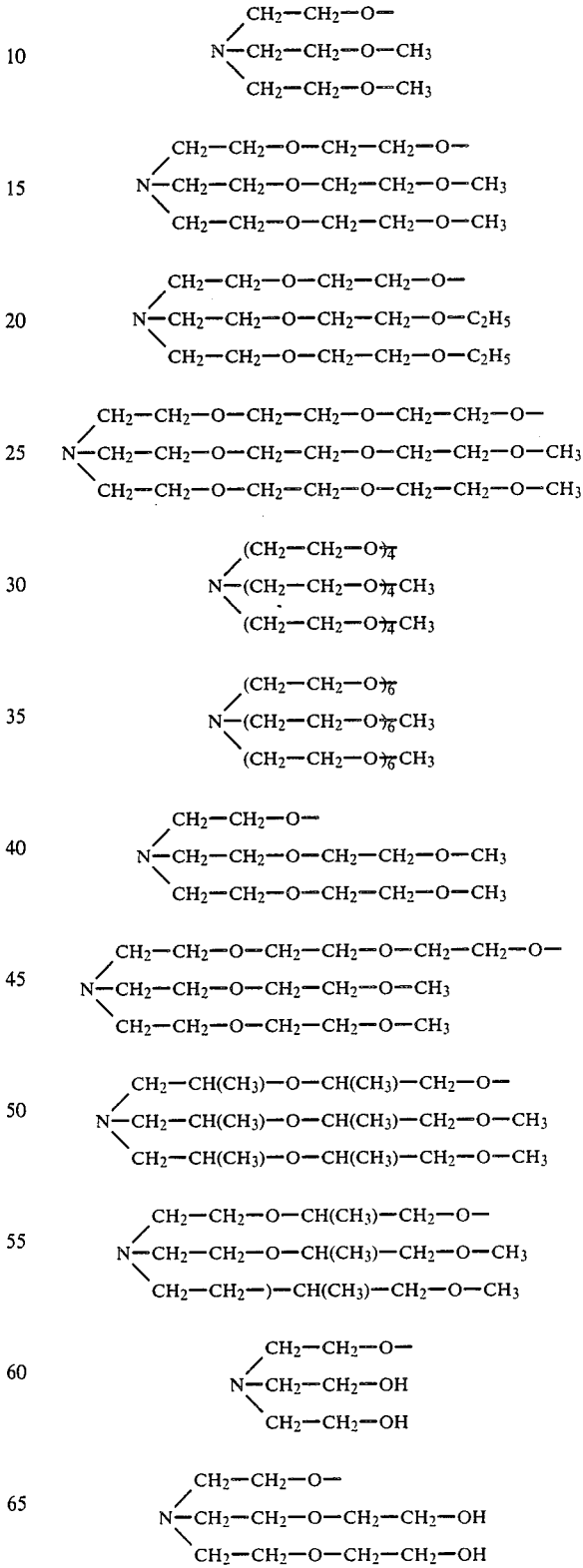

atoms and n', m' and p', which are identical or different, are greater than or equal to 1 and less than or equal to 6.

Examples of functional groups thereon which may be mentioned are those of the following formula:

In another preferred method of practicing the invention, a supported sequestering agent is used which comprises a crosslinked organic polymeric support and a plurality of functional groups, grafted (bound) to said support and of the previously identified general formula (III), in which $R_1'$, $R_2'$, $R_3'$, $R_4'$, $R_6'$ and $R_7'$, which maybe identical or different, represent, most preferably, a hydrogen atom or a methyl group and $R_5'$ and $R_8'$, which may be identical or different, represent a hydrogen atom or an alkyl group having from 1 to 4 carbon -continued

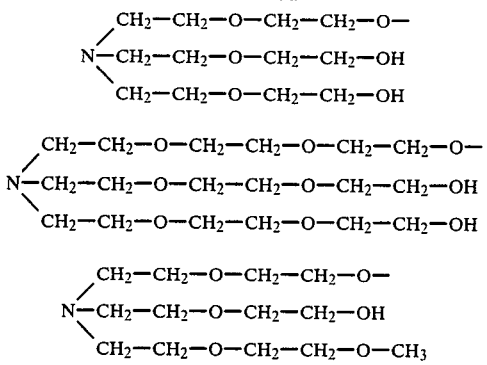

The support for the above functional groups can be derived from any crosslinked organic polymer containing moieties which can be substituted by the functional groups of the formula (III).

Examples of organic polymers suitable as supports in the process of the present invention are polymers derived from vinyl aromatic compounds such as styrene and methylstyrene, and copolymers of vinyl aromatic compounds with $C_4$–$C_6$ conjugated dienes, such as styrene/butadiene and styrene/isoprene copolymers.

Particularly preferred for use in the invention is polystyrene and in a preferred embodiment divinylbenzene is employed therewith as the crosslinking agent. The degree of crosslinking is an important factor inasmuch as it is necessary that the functional groups of the formula (III) grafted onto the polystyrene support be active. Accordingly, the molecules of the solvent in which the supported sequestering agent is to be used in the application of the present invention must penetrate the interstices of the polymer. To achieve this end, the degree of crosslinking must not be so high that it prevents the solvent and the reactants from penetrating and, accordingly, preferred polystyrenes are those with a degree of divinylbenzene crosslinking less than about 10%. Even more preferably, the degree of crosslinking is less than about 5%.

Typical groups which can be substituted with the aforementioned functional groups are the chlorine or the bromine of chloromethyl or bromomethyl groups, i.e., —$CH_2Cl$ or —$CH_2Br$, on the benzene nucleus of the polystyrene. With respect to such substituted benzene moieties, it is particularly preferred for the percentage of benzene nuclei of the polystyrene which carry a functional group to be more than 5% and, even more preferably, more than 10%.

The preferred supported sequestering agents can be represented by the following formula:

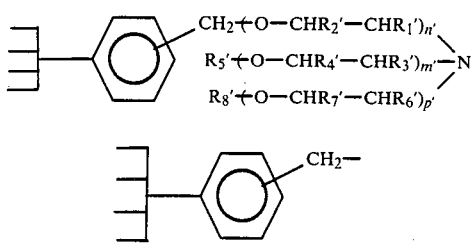

and which are derived from chloromethylated or bromomethylated polystyrene crosslinked by divinylbenzene, of the formula:

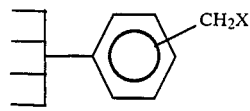

where X represents Cl or Br.

Another preferred embodiment of the invention uses a macrocyclic polyether or a macrocyclic or bicyclic compound grafted onto a crosslinked organic polymer comprising a polystyrene obtained by reacting an appropriate amino derivative, the macrocyclic polyether or the macrocyclic or bicyclic compound with a chloromethylated polystyrene. These preferred supported products can be represented by the following formula:

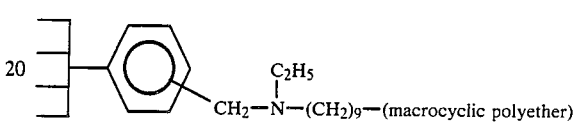

and

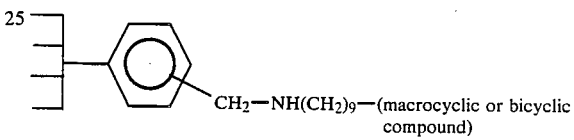

In general, the process according to the invention can be carried out in the presence or absence of solvent(s). In the latter instances, the starting silane acts as the solvent. When an auxiliary solvent is used, although the choice of particular solvent is not critical, the selected solvent should conform to the requirements that it solubilize the starting silane and be chemically inert with respect to the silanes introduced or formed.

Examples of suitable solvents include chlorobenzene, ortho-dichlorobenzene, benzene, toluene, cyclohexane, heptane, dichloroethane, methylene chloride, dichlorobenzene, tetrahydrofuran, dioxane and dimethoxyethane.

The selection of the most suitable complexing compound of those set forth above for carrying out the process according to the invention is generally determined on the basis of the valency and relative size of the cationic portion of the ionic inorganic salt. Generally, the larger the relative size of the cation, the greater the number of oxygen atoms there must be in the molecule of the complexing compound in order to promote sufficient coordinate bonding to complex catalytic anion moiety.

The process according to the invention is preferably carried out at a temperature of the order of ambient temperature, i.e., at between about 0° and 50° C. The capacity to carry out silane disproportionation reactions at low temperatures represents one of the fundamental advantages of the process according to the invention. However, if desired, the process can be carried out at other temperatures, and in particular temperatures of between −30° C. and the boiling point of the reaction medium.

The process is preferably carried out at atmospheric pressure. Although pressures above or below atmospheric pressure are likewise operative.

The complexing compounds of the invention are used in an amount such that the molar ratio of the complexing compound to the ionic inorganic salt is preferably between about 0.05 and 20. Even more preferably, the molar ratio will range between about 0.12 and 2.

The molar ratio of the ionic inorganic salt to the starting silane is preferably between about 1 and 0.0001 and even more preferably, between about 0.5 and 0.005.

The silanes obtained by the disproportionation reaction can either be separated off progressively as they are formed, if they are sparingly soluble in the reaction medium and sufficiently volatile, or separated at the completion of the reaction by techniques well known to those skilled in the art, such as, for example, by distillation, selective solubilization, or the like.

The process according to the invention allows for the facile disproportionation of silanes by accepted conventional methods.

The polymer or copolymer grafted complexing agents used according to the invention make it further possible to carry out the process continuously, on a column, whereas the non-grafted complexing compounds will generally be employed to carry out the process discontinuously.

The present invention thus now makes it possible to carry out the disproportionation of silanes containing at least one Si—H bond, at ambient temperature, with exceptional yield productivity and with the use of reduced amounts of catalyst compared to heretofore known processes.

Other characteristics, features and advantages of the invention will be even more readily comprehended on reading the examples which follow, it being understood that same are intended only as illustrative and in no wise limitative.

EXAMPLE NO. 1

The following are introduced into an 8 ml flask fitted with a Viton septum:

$44.9 \times 10^{-3}$ mol, i.e., 5.050 g, of chlorobenzene as the solvent, $0.255 \times 10^{-3}$ mol, i.e., 10.8 mg, of LiCl as the ionic inorganic salt, and $0.26 \times 10^{-3}$ mol, i.e., 85.7 mg, of tris-(3,6-dioxaheptyl)-amine as the complexing compound capable of at least partially dissociating LiCl. The last mentioned complexing compound will be denoted as TDA 1 hereafter in the remaining examples.

After the flask has been heated to a temperature of 30° C., 3.346 g, $(24.7 \times 10^{-3}$ mol), of $HSiCl_3$ are introduced using a syringe.

The disproportionation reaction of $HSiCl_3$ is followed by periodically analyzing the reaction mixture by gas chromatography.

After a reaction time of 1 hour, the composition is as follows (all percentages here and in the examples which follow relative to this analysis are percentages by weight):

Chlorobenzene: 60.6%
$HSiCl_3$: 38.7%
$SiCl_4$: 0.88%
$H_2SiCl_2$: 0.52% which corresponds to a degree of conversion of the $HSiCl_3$ starting silane of 3.5%.

In a controlled comparative experiment, carried out under the same conditions but without using TDA 1, the formation of $SiCl_4$ and $H_2SiCl_2$ is not detectable, even after about thirty hours or more reaction time.

EXAMPLE NO. 2

The experiment of Example 1 is repeated, except that the molar ratio of (TDA 1+LiCl)/$HSiCl_3$ is increased as shown below.

Chlorobenzene: 5.170 g ($45.9 \times 10^{-3}$ mol)
TDA 1: 252 mg ($0.78 \times 10^{-3}$ mol)
LiCl: 31.8 mg ($0.75 \times 10^{-3}$ mol)
$HSiCl_3$: 3.370 g ($24.9 \times 10^{-3}$ mol)

After a reaction time of 1 hour, the composition is as follows:

Chlorobenzene: 58.35%
$HSiCl_3$: 33.7%
$SiCl_4$: 2.75%
$H_2SiCl_2$: 1.63% which corresponds to a degree of conversion of the $HSiCl_3$ of 11.5%.

The thermodynamic equilibrium (degree of conversion of the $HSiCl_3$ of about 18%) is reached in 2 hours 30 minutes.

EXAMPLE NO. 3

The same experiment is carried out under operating conditions identical to those of the previous examples, except that the molar ratio of (TDA 1+LiCl)/$HSiCl_3$ is again increased:

Chlorobenzene: 5.170 g ($45.9 \times 10^{-3}$ mol)
TDA 1: 420 mg ($1.30 \times 10^{-3}$ mol)
LiCl: 53 mg ($1.25 \times 10^{-3}$ mol)
$HSiCl_3$: 3.370 g ($24.9 \times 10^{-3}$ mol)

After a reaction time of 1 hour, the composition is as follows:

Chlorobenzene: 50.6%
$HSiCl_3$: 31.6%
$SiCl_4$: 4.06%
$H_2SiCl_2$: 2.41% which corresponds to a degree of conversion of the $HSiCl_3$ of 17%.

The thermodyanamic equilibrium is reached in about 1 hour 20 minutes.

EXAMPLE NO. 4

Under operating conditions identical to those of Example No. 1, an $HSiCl_3$ disproportionation reaction is carried out in the presence of the system TDA 1+LiCl, but without a solvent:

TDA 1: 84 mg ($0.26 \times 10^{-3}$ mol)
LiCl: 11 mg ($0.26 \times 10^{-3}$ mol)
$HSiCl_3$: 3.26 g ($24.1 \times 10^{-3}$ mol)

After a reaction time of 1 hour, the composition is as follows:

$HSiCl_3$: 86.5%
$SiCl_4$: 6.70%
$H_2SiCl_2$: 3.99% which corresponds to a degree of conversion of the $HSiCl_3$ of 11%.

EXAMPLE NO. 5

Under operating conditions the same as those of Example No. 1, an $HSiCl_3$ disproportionation reaction is carried out in the presence of the system TDA 1+KCl:

Chlorobenzene: 5.147 g ($45.7 \times 10^{-3}$ mol)
TDA 1: 81 mg ($0.25 \times 10^{-3}$ mol)
KCl: 18.5 mg ($0.25 \times 10^{-3}$ mol)
$HSiCl_3$: 2.998 g ($22.1 \times 10^{-3}$ mol)

After a reaction time of 1 hour, the composition is as follows:

Chlorobenzene: 63.36%

HSiCl$_3$: 32.85%
SiCl$_4$: 2.52%
H$_2$SiCl$_2$: 1.50%
which corresponds to a degree of conversion of the HSiCl$_3$ of 10.9%.

EXAMPLE NO. 6

In this example, the reaction set forth in Example 5 is repeated, but at a temperature of 50° C. instead of 30° C.:
Chlorobenzene: 5.948 g (52.8×10$^{-3}$ mol)
TDA 1: 80 mg (0.25×10$^{-3}$ mol)
KCl: 18.5 mg (0.25×10$^{-3}$ mol)
HSiCl$_3$: 2.548 g (21.8×10$^{-3}$ mol)
After a reaction time of 1 hour, the composition is as follows:
Chlorobenzene: 63.2%
HSiCl$_3$: 28.7%
SiCl$_4$: 1.67%
H$_2$SiCl$_2$: 0.99%
which corresponds to a degree of conversion of the HSiCl$_3$ of 8.5%.

The thermodynamic equilibrium is reached in 4 hours.

EXAMPLE NO. 7

Following the conditions of Example No. 1, an HSiCl$_3$ disproportionation experiment is carried out in a chlorobenzene medium, with LiCl, but the tris-(3,6-dioxaheptyl)-amine (TDA 1) is replaced by the same amine grafted onto polystyrene resin:
Chlorobenzene: 5.538 g (49.2×10$^{-3}$ mol)
TDA 1 grafted onto polystyrene: 163 mg (0.25×10$^{-3}$ mol)
KCl: 18.5 mg (0.25×10$^{-3}$ mol)
HSiCl$_3$: 2.915 g (21.5×10$^{-3}$ mol)
After a reaction time of 1 hour, the composition is as follows:
Chlorobenzene: 64.2%
HSiCl$_3$: 31.5%
SiCl$_4$: 1.37%
H$_2$SiCl$_2$: 0.82%
which corresponds to a degree of conversion of the HSiCl$_3$ of 6.5%.

EXAMPLE NO. 8

Under operating conditions as set forth in Example No. 1, an HSiCl$_3$ disproportionation reaction is carried out in the presence of the system TDA 1+KI, again at 30° C. in a chlorobenzene medium:
Chlorobenzene: 5.240 g (46.6×10$^{-3}$ mol)
TDA 1: 89 mg (0.28×10$^{-3}$ mol)
KI: 45.7 mg (0.28×10$^{-3}$ mol)
HSiCl$_3$: 3.183 g (23.5×10$^{-3}$ mol)
The catalyst system is partially soluble in the solvent (the degree of solubilization of the salt being 43%).
After a reaction time of 2 hours, the composition is as follows:
Chlorobenzene: 62.2%
HSiCl$_3$: 35.5%
SiCl$_4$: 1.40%
H$_2$SiCl$_2$: 0.83%
which corresponds to a degree of conversion of the HSiCl$_3$ of 5.9%.

EXAMPLE NO. 9

Under the operating conditions of Example No. 1, an HSiCl$_3$ disproportionation reaction is carried out in the presence of the system TDA 1+NaI:
Chlorobenzene: 5.293 g (47×10$^{-3}$ mol)
TDA 1: 80.8 mg (0.25×10$^{-3}$ mol)
NaI: 37.5 mg (0.25×10$^{-3}$ mol)
HSiCl$_3$: 3.358 g (24.1×10$^{-3}$ mol)
The catalyst system is totally soluble.
After a reaction time of ½ hour, the composition is as follows:
Chlorobenzene: 61.9%
HSiCl$_3$: 32.4%
SiCl$_4$: 3.59%
H$_2$SiCl$_2$: 2.13%
which corresponds to a degree of conversion of the HSiCl$_3$ of 15%.

The thermodynamic equilibrium (degree of conversion of the HSiCl$_3$ of about 18%) is reached in 1 hour 10 minutes.

EXAMPLE No. 10

In this example, the experiment described in Example No. 9 is repeated, except that the solvent is omitted:
TDA 1: 84 mg (0.26×10$^{-3}$ mol)
NaI: 37.5 mg (0.25×10$^{-3}$ mol)
HSiCl$_3$: 3.437 g (25.4×10$^{-3}$ mol)
The catalyst system is partially soluble in the foregoing reaction medium.
After a reaction time of 1 hour, the composition is as follows:
HSiCl$_3$: 89.7%
SiCl$_4$: 4.25%
H$_2$SiCl$_2$: 2.52%
which corresponds to a degree of conversion of the HSiCl$_3$ of 7.1%.

EXAMPLE NO. 11

Under the experimental conditions described in Example No. 1, an HSiCl$_3$ disproportionation reaction is carried out in the presence of TDA 1+NaBr:
Chlorobenzene: 5.30 g (47.1×10$^{-3}$ mol)
TDA 1: 84 mg (0.25×10$^{-3}$ mol)
NaBr: 25.7 mg (0.25×10$^{-3}$ mol)
The solution obtained is filtered before the introduction of HSiCl$_3$ as follows:
HSiCl$_3$: 3.221 g (23.8×10$^{-3}$ mol)
After a reaction time of 1 hour, the composition is as follows:
Chlorobenzene: 62.2%
HSiCl$_3$: 33.8%
SiCl$_4$: 2.49%
H$_2$SiCl$_2$: 1.48%
which corresponds to a degree of conversion of the HSiCl$_3$ of 10.5%.

The thermodynamic equilibrium is reached in about 3 hours.

EXAMPLE NO. 12

Under the operating conditions described in Example 1, an HSiCl$_3$ disproportionation reaction is carried out in the presence of TDA 1+CsCl:
Chlorobenzene: 5.078 g (45.1×10$^{-3}$ mol)
TDA 1: 86 mg (0.266×10$^{-3}$ mol)
CsCl: 43 mg (0.256×10$^{-3}$ mol)
HSiCl$_3$: 3.185 g (23.5×10$^{-3}$ mol)

After a reaction time of 2 hours, the composition is as follows:
Chlorobenzene: 61.5%
$HSiCl_3$: 35.6%
$SiCl_4$: 1.57%
$H_2SiCl_2$: 0.93%
which corresponds to a degree of conversion of the $HSiCl_3$ of 7.5%.

EXAMPLE NO. 13

Following the reaction conditions of Example No. 1, an $HSiCl_3$ disproportionation reaction is carried out in the presence of TDA 1+$CaCl_2$:
Chlorobenzene: 5.169 g ($45.9 \times 10^{-3}$ mol)
TDA 1: 80.8 mg ($0.25 \times 10^{-3}$ mol)
$CaCl_2$: 27.7 mg ($0.25 \times 10^{-3}$ mol)
The solution obtained is filtered before the $HSiCl_3$ is introduced:
$HSiCl_3$: 3.404 g ($25.1 \times 10^{-3}$ mol)
After a reaction time of 2 hours, the composition is as follows:
Chlorobenzene: 60.8%
$HSiCl_3$: 37.9%
$SiCl_4$: 1.30%
$H_2SiCl_2$: 0.78%
which corresponds to a degree of conversion of the $HSiCl_3$ of 5.2%.

EXAMPLE NO. 14

Under the operating conditions of Example No. 1, an $HSiCl_3$ disproportionation reaction is carried out in the presence of TDA 1+$Na_2CO_3$:
Chlorobenzene: 5.226 g ($46.4 \times 10^{-3}$ mol)
TDA 1: 84 mg ($0.26 \times 10^{-3}$ mol)
$Na_2CO_3$: 27 mg ($0.255 \times 10^{-3}$ mol)
$HSiCl_3$: 3.116 g ($23.8 \times 10^{-3}$ mol)
After a reaction time of 3 hours, the composition is as follows:
Chlorobenzene: 61.8%
$HSiCl_3$: 36.2%
$SiCl_4$: 0.42%
$H_2SiCl_2$: 0.25%
which corresponds to a degree of conversion of the $HSiCl_3$ of 1.8%.

EXAMPLE NO. 15

In this example, the reaction described in Example No. 9 is repeated, except that the chlorobenzene solvent is replaced by cyclohexane:
Cyclohexane: 3.830 g ($45.5 \times 10^{-3}$ mol)
TDA 1: 84 mg ($0.26 \times 10^{-3}$ mol)
NaI: 37.5 mg ($0.25 \times 10^{-3}$ mol)
$HSiCl_3$: 3.316 g ($24.5 \times 10^{-3}$ mol)
After a reaction time of 2 hours, the composition is as follows:
Cyclohexane: 53.3%
$HSiCl_3$: 43.9%
$SiCl_4$: 1.45%
$H_2SiCl_2$: 0.86%
which corresponds to a degree of conversion of the $HSiCl_3$ of 5%.

EXAMPLE NO. 16

In this example, the reaction described in Example No. 9 is repeated, except that benzonitrile is used as the solvent:
Benzonitrile: 4.666 g ($45.2 \times 10^{-3}$ mol)
TDA 1: 84 mg ($0.26 \times 10^{-3}$ mol)
NaI: 37.5 mg ($0.25 \times 10^{-3}$ mol)
$HSiCl_3$: 3.20 g ($23.6 \times 10^{-3}$ mol)
After a reaction time of 2 hours, the composition is as follows:
Benzonitrile: 59.9%
$HSiCl_3$: 38.7%
$SiCl_4$: 1.0%
$H_2SiCl_2$: 0.62%
which corresponds to a degree of conversion of the $HSiCl_3$ of 4.1%.

EXAMPLE NO. 17

In this example, Example No. 5 is repeated, except that the chlorobenzene solvent is replaced by a mixture of chlorobenzene and glycol dimethyl ether:
Chlorobenzene: 1.160 g ($10.3 \times 10^{-3}$ mol)
$(CH_3OCH_2)_2$: 3.190 g ($35.4 \times 10^{-3}$ mol)
TDA 1: 80 mg ($0.25 \times 10^{-3}$ mol)
KCl: 18.5 mg ($0.25 \times 10^{-3}$ mol)
$HSiCl_3$: 2.838 g ($20.9 \times 10^{-3}$ mol)
After a reaction time of 2 hours, the composition is as follows:
Chlorobenzene: 15.9%
$(CH_3OCH_2)_2$: 43.8%
$HSiCl_3$: 35.5%
$SiCl_4$: 2.09%
$H_2SiCl_2$: 1.24%
which corresponds to a degree of conversion of the $HSiCl_3$ of 8.6%.

The thermodynamic equilibrium is reached in about 6 hours.

EXAMPLE NO. 18

In the same manner as Example No. 1, an $HSiCl_3$ disproportionation reaction is carried out at 30° C. in the presence of KCl and 2,5,8,15,18,21-hexaoxatricyclo(20.4.0.0$^{9.14}$)hexacosane, (marketed under the description dicyclohexyl-18-crown-6:
Chlorobenzene: 2.971 g ($26.4 \times 10^{-3}$ mol)
Dicyclohexyl-18-crown-6: 52.1 mg ($0.14 \times 10^{-3}$ mol)
KCl: 10.4 mg ($0.14 \times 10^{-3}$ mol)
$HSiCl_3$: 1.988 g ($14.7 \times 10^{-3}$ mol)
After a reaction time of 24 hours, the composition is as follows:
Chlorobenzene: 60.4%
$HSiCl_3$: 33.3%
$SiCl_4$: 4.49%
$H_2SiCl_2$: 2.67%
which corresponds to a degree of conversion of the $HSiCl_3$ of 17.7% (i.e., thermodynamic equilibrium).

EXAMPLE NO. 19

Using the conditons of Example No. 1, an $HSiCl_3$ disproportionation reaction is carried out in the presence of KCl and 4,7,13,16,21,24-hexaoxa-1,10-diazabicyclo(8,8,8)hexacosane (marketed as Kryptofix 2,2,2 ®):
Chlorobenzene: 3.358 g ($29.8 \times 10^{-3}$ mol)
Kryptofix 2,2,2 ®: 62.8 mg ($0.167 \times 10^{-3}$ mol)
KCl: 12.4 mg ($0.167 \times 10^{-3}$ mol)
$HSiCl_3$: 2.315 g ($17.1 \times 10^{-3}$ mol)
After a reaction time of ½ hour, the composition is as follows:
Chlorobenzene: 59.7%
$HSiCl_3$: 34.0%
$SiCl_4$: 4.52%
$H_2SiCl_2$: 2.69% which corresponds to a degree of conversion of the HSiCl$_3$ of 17.5% (virtually thermodynamic equilibrium).

EXAMPLE NO. 20

In this example, the experiment described in Example No. 19 is repeated, except that the salt KCl is replaced by KI:

Chlorobenzene: 5.049 g (44.9×10$^{-3}$ mol)
Kryptofix 2,2,2 ®: 94.1 mg (0.25×10$^{-3}$ mol)
KI: 41.5 mg (0.25×10$^{-3}$ mol)
HSiCl$_3$: 3.293 g (243×10$^{-3}$ mol)

After a reaction time of ½ hour, the composition is as follows:

Chlorobenzene: 61.2%
HSiCl$_3$: 32.8%
SiCl$_4$: 4.45%
H$_2$SiCl$_2$: 2.65% which corresponds to a degree of conversion of the HSiCl$_3$ of 17.8% (virtually thermodynamic equilibrium).

EXAMPLE NO. 21

Under the same operating conditions as for Example 1, a CH$_3$SiHCl$_2$ disproportionation reaction is carried out in the presence of TDA 1+LiCl, in a chlorobenzene medium, at 30° C.:

Chlorobenzene: 2.228 g (19.8×10$^{-3}$ mol)
TDA 1: 0.352 mg (1.09×10$^{-3}$ mol)
LiCl: 21.8 mg (0.51×10$^{-3}$ mol)
CH$_3$SiHCl$_2$: 0.775 g (6.74×10$^{-3}$ mol)

After a reaction time of 19 hours, the composition is as follows:

Chlorobenzene: 65.4%
CH$_3$SiHCl$_2$: 21.6%
CH$_3$SiCl$_3$: 0.74%
CH$_3$SiH$_2$Cl: 0.40% which corresponds to a degree of conversion of the CH$_3$SiHCl$_2$ of 5%.

While the invention has been described in terms of various preferred embodiments, those skilled in the art will appreciate that various modifications, substitutions, omissions and changes may be made without departing from the spirit thereof. Accordingly, it is intended that the scope of the present invention be limited solely by the scope of the following claims.

What is claimed is:

1. A process for the disproportionation of silanes having at least one Si—H bond which comprises reacting:
   (a) a silane comprising at least one Si—H bond, of the general formula R$_n$H$_m$SiX$_{4-(n+m)}$ wherein R represents an alkyl or aryl group, X represents a halogen or an alkoxy group, n is an integer equal to 0, 1, 2 or 3 and m is an integer equal to 1, 2 or 3, and
   (b) a catalyst system comprising an ionic inorganic salt and a complexing agent which at least partially dissociates said salt and complexes the cation of said salt.

2. A process according to claim 1, wherein the ionic inorganic salt is represented by M$^+$A$^-$ wherein M$^+$ represents an alkali metal, alkaline earth metal or ammonium, and those wherein A$^-$ represents halogen, SCN$^-$, CN$^-$ or CO$_3^{--}$.

3. A process according to claim 2 wherein M$^+$ represents Li$^+$, Na$^+$, K$^+$, Ca$^{++}$, NH$_4^+$ and A$^-$ represents Cl$^-$, Br$^-$, or I$^-$.

4. A process according to claim 1, wherein said complexing agent is a sequestering agent of the formula (I):

$$N-(CHR_1-CHR_2-O-(CHR_3-CHR_4-O)_n-R_5)_3 \quad (I)$$

wherein n is an integer equal to 0 through 10, inclusive, R$_1$, R$_2$, R$_3$ and R$_4$, which may be identical or different, represent hydrogen or alkyl having from about 1 to 4 carbon atoms and R$_5$ represents alkyl or cycloalkyl having from about 1 to 12 carbon atoms, phenyl, or a group of the formula —C$_m$H$_{2m}$-phenyl or —C$_m$H$_{2m+1}$-phenyl-, wherein m is an integer equal to 1 through 12 inclusive.

5. A process according to claim 1, wherein said complexing agent comprises a macrocyclic polyether comprising from about 15 to 30 atoms and 4 to 10 units of the group —O—X in the ring wherein X represents —CHR$_6$—CHR$_7$— or —CHR$_6$—CHR$_8$—CR$_9$R$_7$—, with R$_6$, R$_7$, R$_8$ and R$_9$ being identical or different and represented by hydrogen or an alkyl group having from about 1 to 4 carbon atoms, and wherein at least one of the X groups may be —CHR$_6$—CHR$_8$—CR$_9$R$_7$— when the units —O—X— comprise the group —O—CHR$_6$—CHR$_7$—.

6. A process according to claim 1, wherein said complexing agent is a macrocyclic or bicyclic compound of the general formula IIa or IIb

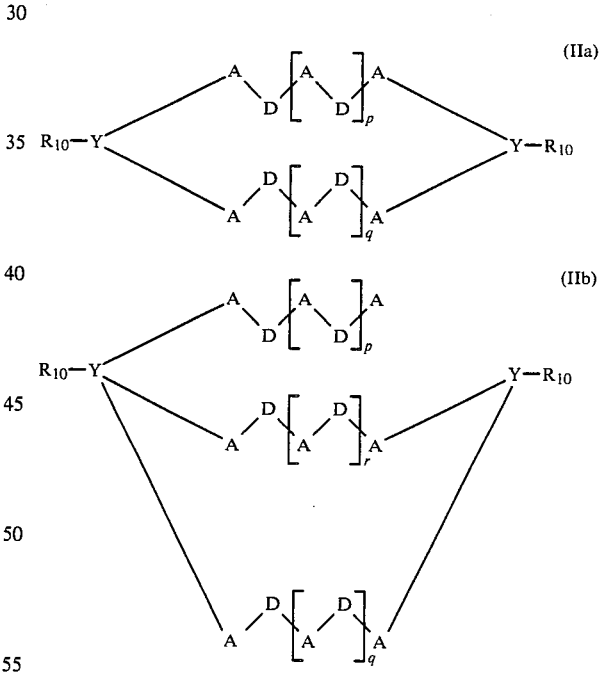

wherein:
Y represents N or P atoms; A represents an alkylene group having from 1 to 3 carbon atoms; D represents O, S or N—R$_{11}$, wherein R$_{11}$ represents an alkyl group having from about 1 to 6 carbon atoms; R$_{10}$ represents an alkyl group having from 1 to 6 carbon atoms; and p, q and r which may be identical or different comprise integers of from 1 through 5 inclusive.

7. A process according to claim 1, wherein said complexing agent is selected from sequestering agents, macrocyclic polyethers and macrocyclic or bicyclic compounds grafted to crosslinked organic polymeric supports.

8. A process according to claim 7, wherein the grafted polymeric sequestering agents comprise a crosslinked organic polymeric support and a plurality of functional groups grafted thereto of the general formula:

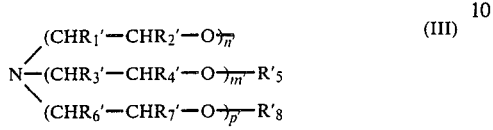

(III)

wherein $R_1'$, $R_2'$, $R_3'$, $R_4'$, $R_6'$ and $R_7'$, which may be identical or different, represent hydrogen, or an alkyl group having from 1 to 4 carbon atoms; $R_5'$ and $R_8'$, which may be identical or different represent hydrogen, alkyl or cycloalkyl having from 1 to 12 carbon atoms; phenyl or the groups $-C_{q'}H_{2q'}$-phenyl or $C_{q'}H_{2q'+1}$-phenyl, with $q'$ being an integer equal to 1 through 12 inclusive, and $n'$, $m'$ and $p'$, which may be identical or different being a integer equal to 1 through 12 inclusive.

9. A process according to claim 4, wherein the sequestering agent of the formula (I) comprises an amine selected from:

tris-(3-oxabutyl)-amine,
tris-(3,6-dioxaheptyl)-amine,
tris-(3,6,9-trioxadecyl)-amine,
tris-(3,6-dioxaoctyl)-amine,
tris-(3,6,9-trioxaundecyl)-amine,
tris-(3,6-dioxanonyl)-amine,
tris-(3,6,9-trioxadodecyl)-amine,
tris-(3,6-dioxadecyl)-amine,
tris-(3,6,9-trioxatridecyl)-amine,
tris-(3,6,9,12-tetraoxatridecyl)-amine,
tris-(3,6,9,12,15,18-hexaoxanonadecyl)-amine,
tris-(3,6-dioxa-4-methylheptyl)-amine, and
tris-(3,6,-dioxa-2,4-dimethylheptyl)-amine.

10. A process according to claim 5, wherein the macrocyclic polyether is selected from compounds represented by

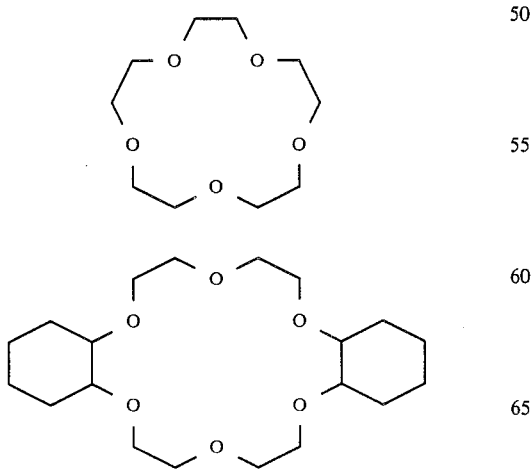

11. A process according to claim 6, wherein the macrocyclic or bicyclic compound is selected from compounds represented by

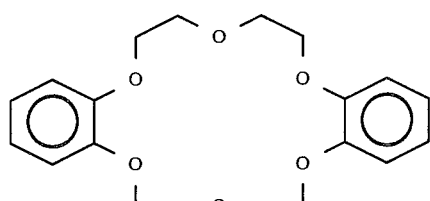

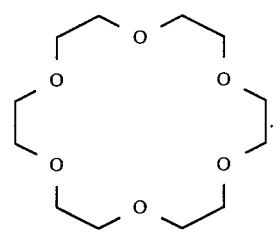

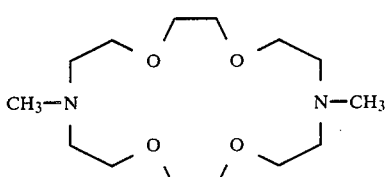

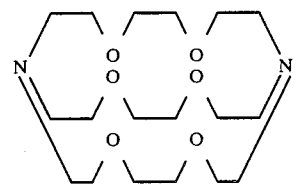

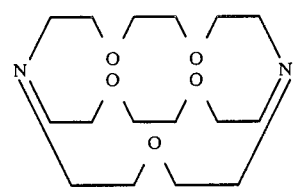

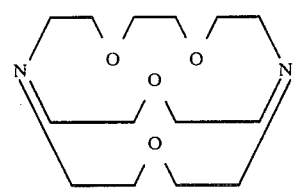

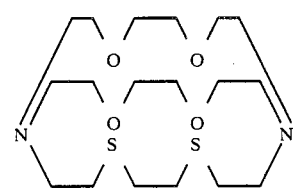

-continued

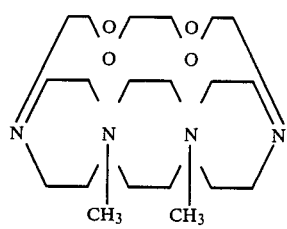

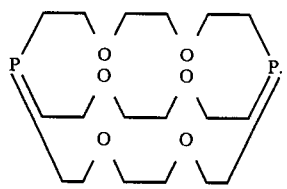

12. A process according to claim 8, wherein the functional groups of the graft sequestering agents are represented by

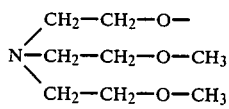

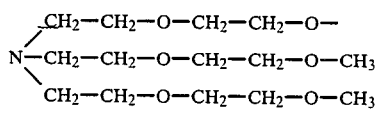

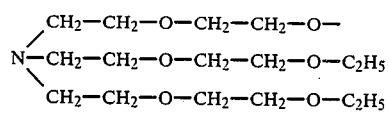

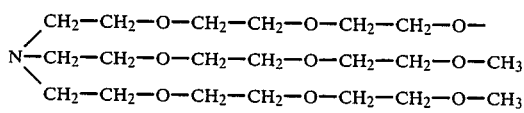

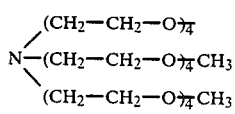

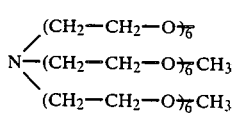

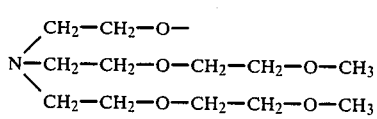

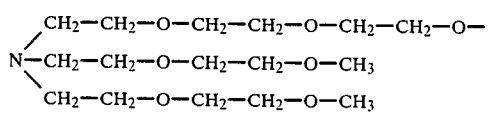

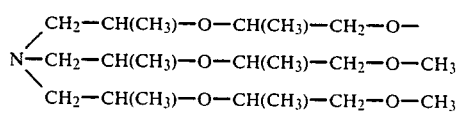

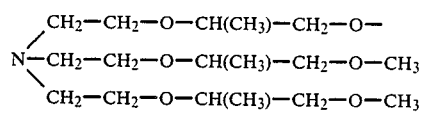

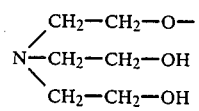

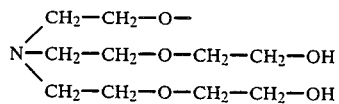

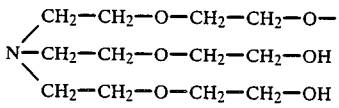

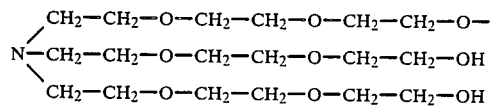

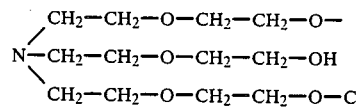

13. A process according to claim 7, wherein the organic polymeric supports are selected from polymers derived from vinylaromatic compounds and copolymers of vinylaromatic compounds with $C_4$-$C_6$ conjugated dienes.

14. A process according to claim 13, wherein said vinylaromatic compounds are selected from styrene and methylstyrene and said conjugated dienes are selected from butadiene and isoprene.

15. A process according to claim 1, wherein the molar ratio of the complexing agent to the ionic inorganic salt is between about 0.05 and 20.

16. A process according to claim 14, wherein the molar ratio of the complexing agent to the ionic inorganic salt is between about 0.12 and 2.

17. A process according to claim 1, wherein the molar ratio of the ionic inorganic salt to the starting silane is between about 1 and 0.0001.

18. A process according to claim 16, wherein the molar ratio of the ionic inorganic salt to the starting silane is between about 0.5 and 0.005.

19. A catalyst system for catalyzing the disproportionation of silanes having at least one Si-H bond comprising an ionic inorganic salt and a complexing agent capable of at least partially dissociating said salt and complexing the cationic moiety of said salt.

20. A catalyst system according to claim 19, wherein the ionic inorganic salt is represented by the formula $M^+A^-$ wherein $M^+$ represents an alkali metal, alkaline earth metal or ammonium and $A^-$ represent halogen, $SCN^-$, $CN^-$ or $CO_3^{--}$.

21. A catalyst system according to claim 19, wherein said complexing agent is selected from amine sequestering agents, macrocyclic polyethers, or macrocyclic or bicyclic compounds optionally grafted to crosslinked polymeric supports.

* * * * *